United States Patent
Stefinovic et al.

(10) Patent No.: US 10,206,916 B2
(45) Date of Patent: Feb. 19, 2019

(54) CABOZANTINIB SALTS AND THEIR USE AS ANTI-CANCER AGENTS

(71) Applicant: Sandoz AG, Basel (CH)

(72) Inventors: Marijan Stefinovic, Kundl (AT); Erwin Paul Schreiner, Kundl (AT)

(73) Assignee: Sandoz AG, Basel (CH)

(*) Notice: Subject to any disclaimer, the term of this patent is extended or adjusted under 35 U.S.C. 154(b) by 0 days.

(21) Appl. No.: 15/560,519

(22) PCT Filed: Mar. 22, 2016

(86) PCT No.: PCT/EP2016/056262
§ 371 (c)(1),
(2) Date: Sep. 22, 2017

(87) PCT Pub. No.: WO2016/150963
PCT Pub. Date: Sep. 29, 2016

(65) Prior Publication Data
US 2018/0110769 A1    Apr. 26, 2018

(30) Foreign Application Priority Data
Mar. 25, 2015 (EP) ..................................... 15160877

(51) Int. Cl.
| | | |
|---|---|---|
| *A61K 31/47* | (2006.01) |
| *A61P 35/00* | (2006.01) |
| *C07D 215/20* | (2006.01) |
| *C07D 215/22* | (2006.01) |

(52) U.S. Cl.
CPC .............. *A61K 31/47* (2013.01); *A61P 35/00* (2018.01); *C07D 215/20* (2013.01); *C07D 215/22* (2013.01)

(58) Field of Classification Search
CPC ..... A61K 31/47; C07D 215/20; C07D 215/22
See application file for complete search history.

(56) References Cited

FOREIGN PATENT DOCUMENTS

| | | |
|---|---|---|
| CN | 104109124 | 10/2014 |
| WO | 2005030410 A2 | 4/2005 |
| WO | 2010083414 A1 | 7/2010 |

OTHER PUBLICATIONS

International Search Report and Written Opinion for PCT/EP2016/056262, dated Sep. 29, 2016.

*Primary Examiner* — Brenda L Coleman
(74) *Attorney, Agent, or Firm* — Luedeka Neely Group, P.C.

(57) ABSTRACT

The present invention relates to crystalline forms of cabozantinib succinate (Form A) and cabozantinib acetate (Form A-1) and to pharmaceutical compositions comprising said crystalline forms and their use as anti-cancer medicaments.

10 Claims, 8 Drawing Sheets

CABOZANTINIB SALTS AND THEIR USE AS ANTI-CANCER AGENTS

This application is a Section 371 national phase entry of PCT application PCT/EP2016/056262, filed Mar. 22, 2016. This application also claims the benefit of the earlier filing date of European patent application 15160877.5, filed Mar. 25, 2015.

FIELD OF THE INVENTION

The present invention relates to crystalline forms of cabozantinib succinate and cabozantinib acetate and to a method for their preparation. Furthermore, the invention relates to pharmaceutical compositions comprising said crystalline forms and their use as anti-cancer medicaments.

BACKGROUND OF THE INVENTION

N-{4-[(6,7-dimethoxy-4-quinolinyl)oxy]phenyl}-N'-(4-fluorophenyl)-1,1-cyclopropanedicarboxamide (international non-proprietary name (INN): cabozantinib) represented by chemical structure

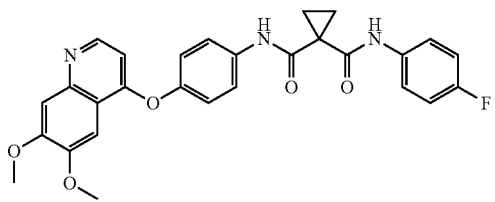

Cabozantinib is a RET, MET, KIT and VEGFR2 receptor tyrosine kinase inhibitor. It is currently marked for the treatment of thyroid cancer under the brand name Cometriq. Cometriq capsules contain cabozantinib as its (L)-malate salt. Cabozantinib is classified as a BCS class II compound having a low solubility and high permeability. The malate salt shows an enhanced solubility when compared with cabozantinib free base.

The above mentioned compound will be referred to in the present application by its international non-proprietary names, i.e. cabozantinib. A salt of cabozantinib will be referred to as cabozantinib salt e.g. cabozantinib succinate or cabozantinib succinic acid salt.

International patent application WO2005/030140 discloses cabozantinib. Further the application discloses processes for the preparation of cabozantinib, pharmaceutical preparation of cabozantinib and therapeutic application thereof.

Patent application CN 104109124 discloses a cabozantinib 0.5 malate crystal, pharmaceutical compositions and therapeutic applications thereof for the treatment of tumor associated diseases. The crystal is characterized by a power X-ray diffraction pattern comprising the diffraction peaks at 2theta angles: 5.48, 10.88, 15.24, 21.97, 24.56 when measured using Cu-Kalpha radiation.

International patent application WO2010/083414 discloses the (L)-, (D)- and (D,L)-malate salts as compounds (I), (II) and (III). WO2010/083414 further discloses the polymorphic Forms N-1 and N-2 of compounds (I) (II) and (III). The (L)-malate salt is reported to be non-hygroscopic and having chemical stability.

Example 1 of WO2010/083414 provides a concrete process for the preparation of cabozantinib free base. Example 2 provides a concrete process for the preparation of cabozantinib (L)-malate crystalline Form N-1 comprising a final crystallization step from acetonitrile as the solvent. The XRPD spectrum of (L)-malate crystalline Form N-1 is also disclosed. Example 4 provides a concrete process for the preparation of cabozantinib (L)-malate crystalline Form N-2 comprising a final crystallization step from a binary system of solvents wherein the solvents are tetrahydrofuran and methyl isobutyl ketone. Seeds are required for crystallization of Form N-2. The XRPD spectrum of (L)-malate crystalline Form N-2 is also disclosed. Form N-2 has been selected for commercial development.

Hence, the cabozantinib (L)-malate salt exists in two polymorphic forms that need to be controlled in the formulation of the drug. WO2010/083414 discloses in Table 1 on page 9 that there was no salt formation between cabozantinib and acetic acid or succinic acid.

In view of the above mentioned drawbacks, there is the need to provide forms of cabozantinib with physicochemical properties which render them suitable for pharmaceutical formulation; in particular solid forms with a balanced profile of appropriate physicochemical properties such as suitable solubility, chemical stability, favorable morphology, improved filterability, appropriate hygroscopicity. There is, as well, the need for pharmaceutical compositions comprising the same.

SUMMARY OF THE INVENTION

The present invention relates to crystalline non-hygroscopic and anhydrous salt forms of cabozantinib with low molecular weight organic acids.

The present invention relates to cabozantinib succinate salt and cabozantinib acetate salt and crystalline forms thereof. These crystalline forms of the invention are anhydrous and non-hygroscopic. They show chemical as well as physical stability and/or appropriate solubility. Furthermore, the crystalline forms of the present invention comprise crystals with especially suitable morphology for the production of pharmaceutical drug products and which can be easily filtered.

Definitions

In the context of the present invention the following abbreviations have the indicated meaning, unless explicitly stated otherwise:

XRPD powder X-ray diffraction/diffractogram
TG/DTA thermogravimetric/differential thermal analysis
DVS dynamic vapor sorption
PLM polarized light microscopy
NMR nuclear magnetic resonance
HPLC-UV High performance liquid chromatography-ultraviolet detection
RT room temperature
RH relative humidity
m mass
Δm mass change
hr heating rate
$\Delta H_{fus}$ difference between the heats of fusion As used herein the term "room temperature" relates to temperatures between 15 and 25° C. [see e.g. European Pharmacopoeia 8.3, (2015)].

As used herein, the term "mother liquor" refers to the solution remaining after crystallization of a solid.

The term "non-hygroscopic" as used herein refers to compounds showing a weight gain of less than 2 weight-% based on the weight of the compound when measured in the range of from 20 to 70% relative humidity at (25.0±0.1)° C.

The term "essentially the same" with reference to XRPD means that variability in peak positions and relative intensities of the peaks are to be taken into account. For example, a typical precision of the 2-Theta values is in the range of ±0.2° 2-Theta. Thus, a diffraction peak that usually appears at 14.9° 2-Theta for example can appear between 14.7° and 15.1° 2-Theta on most X-ray diffractometers under standard conditions. Furthermore, one skilled in the art will appreciate that relative peak intensities will show inter-apparatus variability as well as variability due to degree of crystallinity, preferred orientation, sample preparation and other factors known to those skilled in the art and should be taken as qualitative measure only. Typically, XRPD measurements are done at a temperature of 20° C., preferably also at a relative humidity of 40%.

The term "Form N-1" as used herein refers to the crystalline form of cabozantinib (L)-malate disclosed in WO 2010/083414 A1 which is characterized by having a XRPD comprising reflections at 2-Theta angles of (12.8±0.2°), (13.5±0.2°), (16.9±0.2°), (19.4±0.2°), (21.5±0.2°), (22.8±0.2°), (25.1±0.2°), (26.6±0.2°), when measured at room temperature with Cu-Kalpha radiation having a wavelength of 0.15419 nm. Alternatively, Form N-1 as used herein refers to the form of cabozantinib (L)-malate disclosed in paragraph [0056] pages 10 to 11 of WO2010/083414.

The term "Form N-2" as used herein refers to the crystalline form of cabozantinib (L)-malate disclosed in WO 2010/083414 A1 which is characterized by having a XRPD comprising four or more reflections at 2-Theta angles selected from (6.4±0.2°), (9.1±0.2°), (12.0±0.2°), (12.8±0.2°), (13.7±0.2°), (17.1±0.2°), (20.9±0.2°), (21.9±0.2°), (22.6±0.2°), (23.7±0.2°), when measured at room temperature with Cu-Kalpha radiation having a wavelength of 0.15419 nm. Alternatively, Form N-2 as used herein refers to the form of cabozantinib (L)-malate disclosed in paragraph [0058] page 11 of WO2010/083414.

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the mentioned diffraction angles. Consequently, it is to be understood that the crystal forms of the present invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

The term "cabozantinib succinate salt" means a salt between cabozantinib and succinic acid. Succinic acid is a dicarbonic acid and can form hydrogensuccinate, i.e. a monoanion where one of the two carbonic acid moieties is deprotonated, and succinates, i.e. a dianion where both carbonic acid moieties are deprotonated. Salts with both forms of deprotonated succinic acid are included in the general term "succinate salt" as used herein.

As used herein, the term "substantially pure" with reference to a particular polymorphic form of a salt means that the polymorphic form includes less than 10%, preferably less than 5%, more preferably less than 3%, most preferably less than 1% by weight of any other physical forms of the salt.

DETAILED DESCRIPTION OF THE INVENTION

Figure 1:
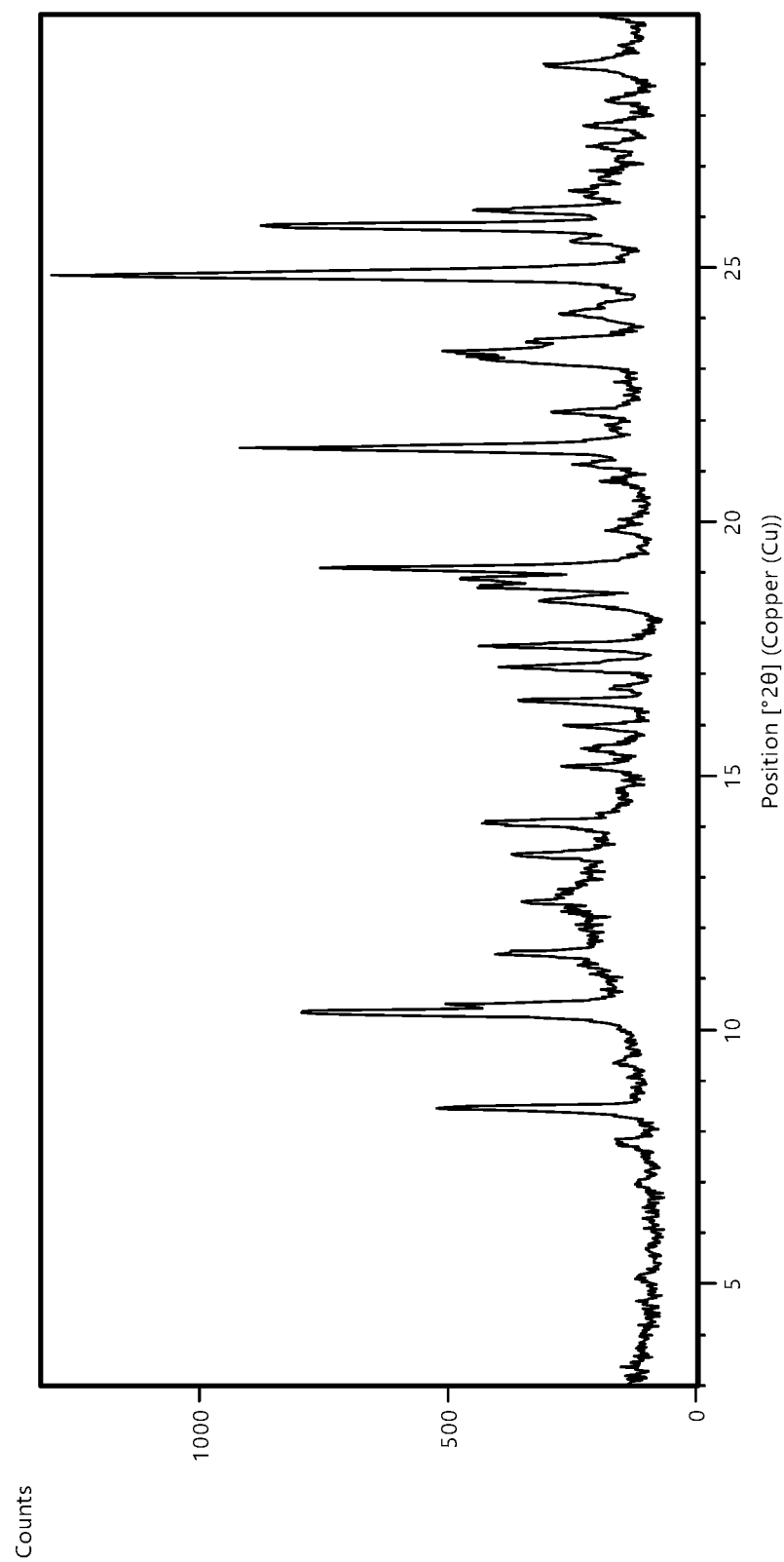
FIG. 1: Representative XRPD of the crystalline Form A of cabozantinib succinate according to the present invention

The invention is described below in further details, without being limited thereto.

Cabozantinib Succinate and Cabozantinib Acetate

The present invention relates to salts of cabozantinib with succinic acid and acetic acid, respectively. In particular, the present invention relates to cabozantinib succinate and cabozantinib acetate.

Preferably in the cabozantinib succinate the molar ratio of cabozantinib relative to the succinate is in the range of from 1:0.5 to 1:2, more preferably from 1:0.7 to 1:1.5 and most preferably from 1:0.8 to 1:1.2.

Preferably in the cabozantinib acetate the molar ratio of the cabozantinib relative to the acetate is in the range of from 1:0.5 to 1:2, more preferably from 1:0.7 to 1:1.5 and most preferably from 1:0.8 to 1:1.2.

Crystalline Forms of Cabozantinib Succinate and Cabozantinib Acetate

The present invention relates to crystalline forms of cabozantinib succinate and cabozantinib acetate.

Preferably, the present invention relates to a crystalline form of cabozantinib succinate, hereinafter also designated as "Form A".

Alternatively, the present invention relates to a crystalline form of cabozantinib acetate, hereinafter also designated as "Form A-1".

Form A and Form A-1 may be characterized by analytical methods well known in the field of the pharmaceutical industry for characterizing solids. Such methods comprise but are not limited to XRPD, TG/DTA, $^1$H NMR, KF and DVS. Form A and Form A-1 may be characterized by one of the aforementioned analytical methods or by combining two or more of them. In particular, Form A and Form A-1 may be characterized by any one of the following aspects or by combining two or more of the following aspects.

Form A and Form A-1 of the present invention can for example be characterized by their XRPD. Table 1 provides reflections for Form A and Form A-1, whereat one or more of these reflections may be used to distinguish the crystalline form.

TABLE 1

Table 1: Form A and Form A-1 reflections

| Form A Reflections [±0.2 °2Th.] | Form A-1 Reflections [±0.2 °2Th.] |
|---|---|
| 5.1 | 11.3 |
| 7.0 | 12.4 |
| 7.8 | 14.2 |
| 8.5 | 14.4 |
| 9.4 | 14.8 |
| 10.4 | 15.4 |
| 10.5 | 15.7 |
| 11.5 | 161 |
| 12.5 | 17.4 |
| 13.4 | 17.6 |
| 14.1 | 18.0 |
| 15.2 | 18.4 |
| 15.5 | 19.4 |
| 16.0 | 21.5 |
| 16.5 | 21.8 |
| 16.7 | 22.6 |
| 17.1 | 22.8 |
| 17.5 | 23.2 |
| 18.4 | 23.7 |
| 18.7 | 24.1 |
| 18.9 | 24.5 |
| 19.1 | 24.9 |
| 19.8 | 25.5 |
| 20.8 | 25.9 |
| 21.1 | 27.6 |
| 21.4 | 27.8 |
| 21.9 | 28.7 |
| 22.2 | 29.1 |
| 23.2 | 29.8 |
| 23.4 | |
| 23.6 | |
| 24.1 | |
| 24.8 | |
| 25.5 | |
| 25.8 | |
| 26.1 | |
| 27.4 | |
| 27.8 | |
| 28.3 | |
| 29.0 | |

Cabozantinib Succinate Form A

Preferably, cabozantinib succinate Form A is characterized by having a XRPD comprising reflections at 2-Theta angles of (8.5±0.2°), (10.4±0.2°), (19.1±0.2°), (21.4±0.2°), (24.8±0.2°), when measured at 20° C. with Cu-Kalpha radiation having a wavelength of 0.15419 nm.

More preferably, cabozantinib succinate Form A is characterized by having a XRPD comprising reflections at 2-Theta angles of (8.5±0.2°), (10.4±0.2°), (19.1±0.2°), (21.4±0.2°), (24.8±0.2°), (25.8±0.2°) when measured at 20° C. with Cu-Kalpha radiation having a wavelength of 0.15419 nm.

Particularly, cabozantinib succinate Form A is characterized by having a XRPD comprising additional reflections at one or more 2-Theta angles selected from the group of (8.5±0.2°), (10.4±0.2°), (19.1±0.2°), (21.4±0.2°), (23.4±0.2°), (24.8±0.2°), (25.8±0.2°) when measured at 20° C. with Cu-Kalpha radiation having a wavelength of 0.15419 nm.

Alternatively, cabozantinib succinate Form A is characterized by having a XRPD comprising reflections at five or more 2-Theta angles selected from the group of (8.5±0.2°), (10.4±0.2°), (19.1±0.2°), (21.4±0.2°), (23.2±0.2°), (23.4±0.2°), (24.8±0.2°), (25.8±0.2°), when measured at 20° C. with Cu-Kalpha radiation having a wavelength of 0.15419 nm.

Alternatively, cabozantinib succinate Form A can be characterized by showing a XRPD which is essentially the same as displayed in FIG. 1 of the present invention, when measured at 20° C. with Cu-Kalpha radiation having a wavelength of 0.15419 nm.

Alternatively or additionally, cabozantinib succinate Form A is characterized by having a TG/DTA curve showing a weight loss of at most 1.2%, preferably of at most 0.8%, when measured at a temperature in the range of from about 25 to 173° C. and a heating rate of about 10° C./min.

Figure 2:
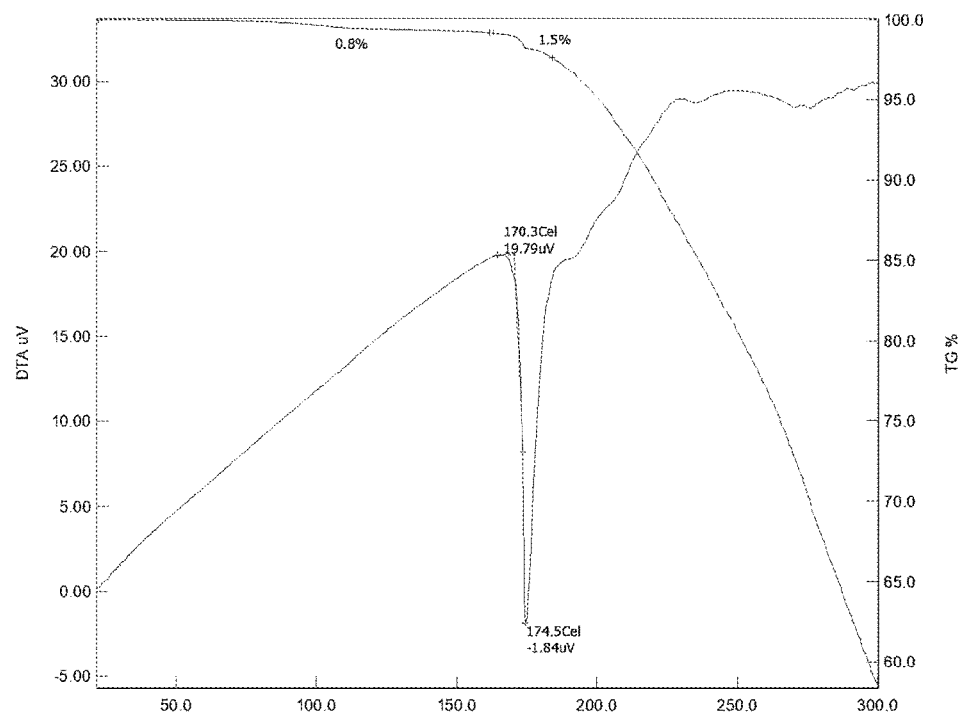
FIG. 2: Representative TG/DTA curve of the crystalline Form A of cabozantinib succinate according to the present invention.

Alternatively or additionally, cabozantinib succinate Form A is characterized by showing a TG/DTA curve essentially the same as displayed in FIG. 2 of the present invention, when measured at a temperature in the range of from about 25 to 173° C. and a heating rate of about 10° C./min Based on the TG/DTA cabozantinib succinate Form A is an anhydrous salt form.

Alternatively or additionally, cabozantinib succinate Form A is characterized by showing a weight gain of at most 0.2%, preferably at most 0.1%, based on the weight of Form A as determined by DVS sorption in the range of from 20% to 70% relative humidity at a temperature of (25.0±0.1)° C.

Figure 3:
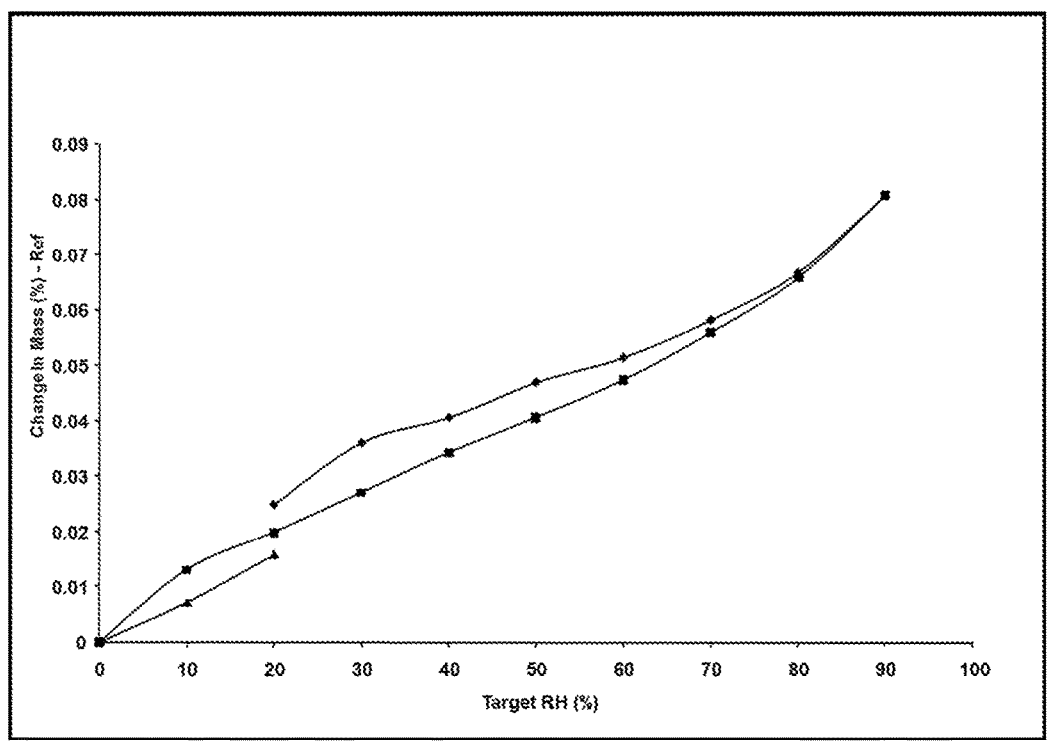
FIG. 3: Representative DVS isotherm of the crystalline Form A of cabozantinib succinate according to the present invention.

Alternatively or additionally, cabozantinib succinate Form A can be characterized by showing a DVS sorption essentially the same as displayed in FIG. 3 of the present invention, when measured at a temperature at of (25.0±0.1)° C.

Furthermore, cabozantinib succinate Form A is characterized as being non-hygroscopic as determined by DVS in the range of from 20% to 70% relative humidity at a temperature of (25.0±0.1)° C.

Still further, cabozantinib succinate Form A is characterized as being a non-solvated crystalline form, preferably an anhydrous crystalline form and most preferably a non-solvated and anhydrous crystalline form.

Preferably, cabozantinib succinate Form A has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form of cabozantinib succinate Form A having substantially pure phase homogeneity with less than 1% of the total peak area in the experimentally measured PXRD pattern arising from the extra peaks that are absent from the simulated PXRD pattern.

In one embodiment, a composition is provided consisting essentially of the cabozantinib succinate form A. The composition of this embodiment may comprise at least 90 weight % of cabozantinib succinate form A, based on the weight of cabozantinib succinate in the composition.

The presence of more than one polymorph in a sample may be determined by techniques such as x-ray powder diffraction (PXRD) or solid state nuclear magnetic resonance spectroscopy. For example, the presence of extra peaks in the comparison of an experimentally measured PXRD pattern with a simulated PXRD pattern may indicate more than one polymorph in the sample. The simulated PXRD may be calculated from single crystal x-ray data. see Smith, D. K., "A FORTRAN Program for Calculating X-Ray Powder Diffraction Patterns," Lawrence Radiation Laboratory, Livermore, Calif., UCRL-7196 (Apr. 1963) or TOPAS program (Total Pattern Analysis Solution, available through Brucker AXS Inc.).

Preferably in the crystalline cabozantinib succinate Form A, the molar ratio of the cabozantinib relative to the succinate is in the range of from 1:0.5 to 1:2, more preferably from 1:0.7 to 1:1.5 and most preferably from 1:0.8 to 1:1.2.

Cabozantinib Acetate Form A-1

Preferably, cabozantinib acetate Form A-1 is characterized by having a XRPD comprising reflections at 2-Theta angles (11.3±0.2°), (12.4±0.2°), (15.4±0.2°), when measured at room temperature with Cu-Kalpha radiation having a wavelength of 0.15419 nm.

More preferably, cabozantinib acetate Form A-1 is characterized by having a XRPD comprising reflections at 2-Theta angles of (11.3±0.2°), (12.4±0.2°), (15.4±0.2°), (24.5±0.2°), when measured at room temperature with Cu-Kalpha radiation having a wavelength of 0.15419 nm.

Particularly, cabozantinib acetate Form A-1 is characterized by having a XRPD comprising additional reflections at one or more 2-Theta angles selected from the group of (11.3±0.2°), (12.4±0.2°), (15.4±0.2°), (22.6±0.2°), (24.5±0.2°) when measured at room temperature with Cu-Kalpha radiation having a wavelength of 0.15419 nm.

Alternatively, cabozantinib acetate Form A-1 is characterized by having a XRPD comprising reflections at five or more 2-Theta angles selected from the group of (11.3±0.2°), (12.4±0.2°), (15.4±0.2°), (21.5±0.2°), (22.6±0.2°), (24.5±0.2°) when measured at room temperature with Cu-Kalpha radiation having a wavelength of 0.15419 nm.

Particularly, cabozantinib acetate Form A-1 is characterized by having a XRPD comprising reflections at five or more 2-Theta angles selected from the group of Form A-1 reflections as listed in table 1, when measured at room temperature with Cu-Kalpha radiation having a wavelength of 0.15419 nm.

Particularly, cabozantinib acetate Form A-1 is characterized by having a XRPD comprising reflections at eight or more, such as ten or more, 2-Theta angles selected from the group of Form A-1 reflections as listed in table 1, when measured at room temperature with Cu-Kalpha radiation having a wavelength of 0.15419 nm.

Figure 4:
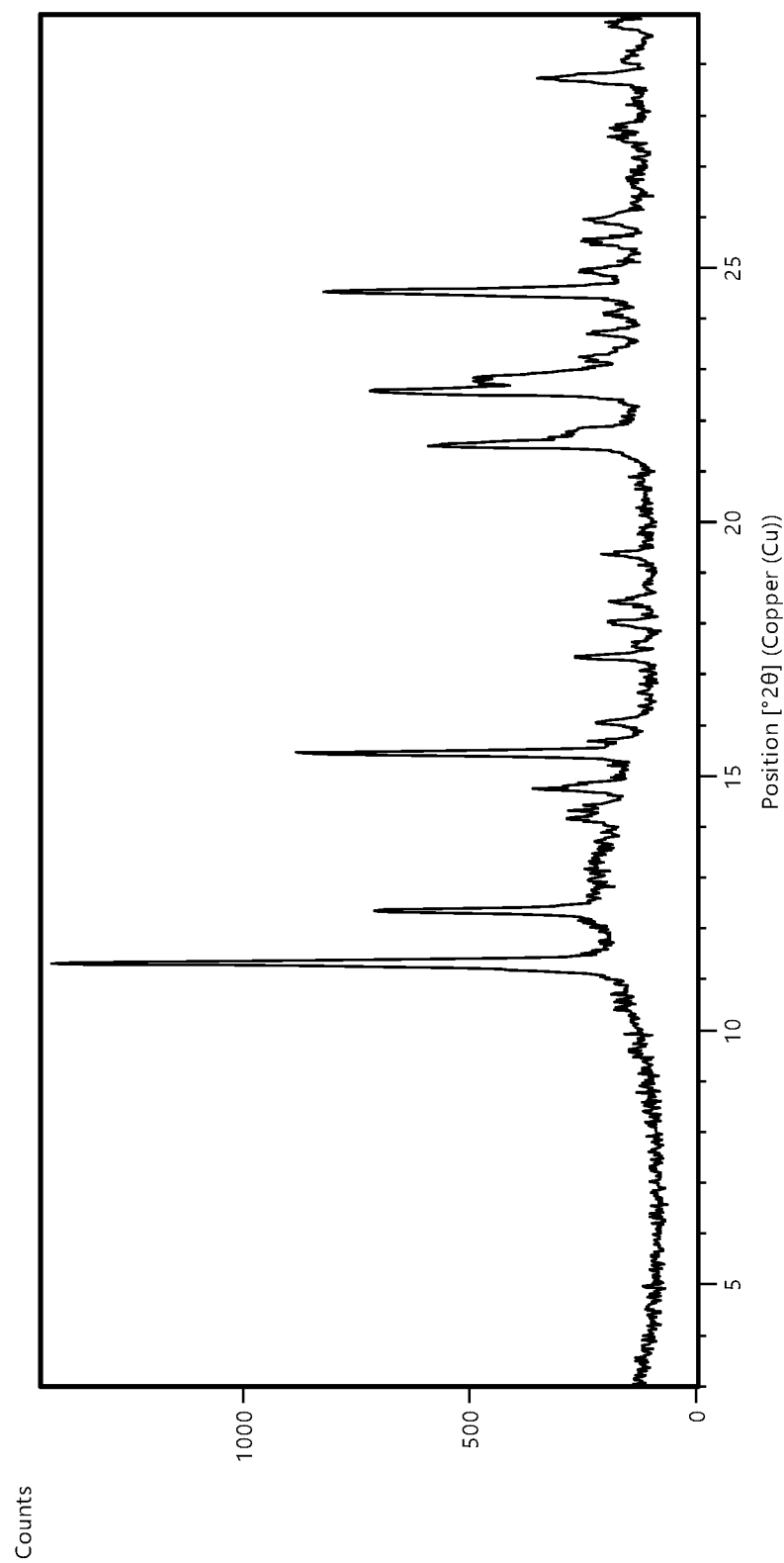
FIG. 4: Representative XRPD of the crystalline Form A-1 of cabozantinib acetate according to the present invention.

Alternatively, cabozantinib acetate Form A-1 can be characterized by showing a XRPD essentially the same as displayed in FIG. 4 of the present invention, when measured at room temperature with Cu-Kalpha radiation having a wavelength of 0.15419 nm.

Alternatively or additionally, cabozantinib acetate Form A-1 can be characterized by showing a weight gain of at most 0.3%, preferably of at most 0.25% based on the weight of cabozantinib acetate Form A-1 as determined by DVS in the range of from 20 to 70% relative humidity at a temperature of (25.0±0.1)° C.

Figure 6:
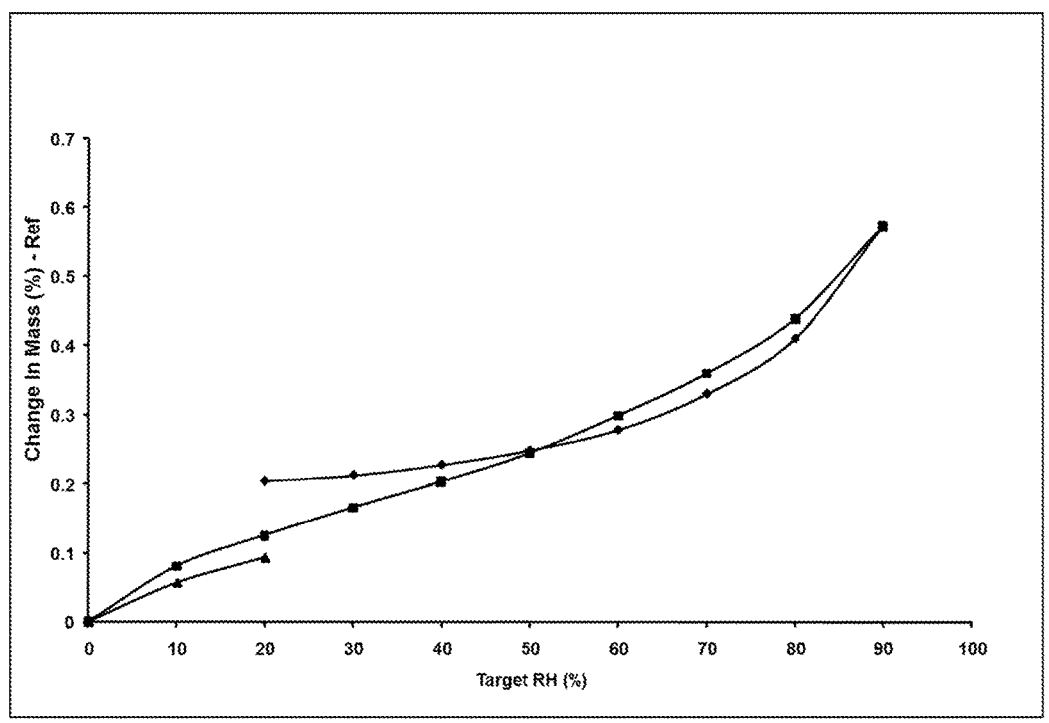
FIG. 6: Representative DVS isotherms the crystalline Form A-1 of cabozantinib acetate according to the present invention

Alternatively or additionally, cabozantinib acetate Form A-1 can be characterized by showing a DVS sorption essentially the same as displayed in FIG. 6 of the present invention, when measured at a temperature of (25.0±0.1)° C., in particular when measured according to reference example C.

Preferably, cabozantinib acetate Form A-1 has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form of cabozantinib acetate Form A-1 having substantially pure phase homogeneity with less than 1% of the total peak area in the experimentally measured PXRD pattern arising from the extra peaks that are absent from the simulated PXRD pattern.

In one embodiment, a composition is provided consisting essentially of the cabozantinib acetate form A-1. The composition of this embodiment may comprise at least 90 weight % of cabozantinib acetate form A-1, based on the weight of cabozantinib acetate in the composition.

Preferably in the crystalline cabozantinib acetate Form A-1, the molar ratio of the cabozantinib relative to the acetate is in the range of from from 1:0.5 to 1:2, more preferably from 1:0.7 to 1:1.5 and most preferably from 1:0.8 to 1:1.2.

Preparation of Cabozantinib Salts and Crystalline Forms Thereof

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture.

Crystals of drugs, including polymorphs, methods of preparation, and characterization of drug crystals are discussed in Solid-State Chemistry of Drugs, S. R. Byrn, R. R. Pfeiffer, and J. G. Stowell, 2nd Edition, SSCI, West Lafayette, Ind. (1999).

The present invention relates to a process for the preparation of crystalline cabozantinib succinate Form A and cabozantinib actetate Form A-1 as disclosed above.

Cabozantinib free base is typically used as the starting material. Cabozantinib free base can, for example, be prepared according WO 2005/030140, preparative example 48, or WO 2010/083414, preparative 1.6.

The process comprises:
(i) combining cabozantinib and a solvent comprising acetone, obtaining a mixture (i);
(ii) combining an acid selected from succinic acid and acetic acid, and a solvent comprising tetrahydrofurn, obtaining a mixture (ii); and
(iii) combining the mixture (i) with the mixture (ii) and obtaining a mixture (iii);
(iv) subjecting the mixture (iii) to temperature cycling, obtaining a mixture comprising a crystalline form of the present invention.

Hence, in (ii) the acid is succinic acid when crystalline cabozantinib succinate form A is to be obtained or the acid is acetic acid when crystalline cabozantinib acetate form A-1 is to be obtained.

Hence, in (iv) the crystalline form obtained is cabozantinib succinate Form A or cabozantinib acetate Form A-1.

Preferably, the molar ratio of cabozantinib in (i) relative to the acid in (ii) is in the range of from 1:0.6 to 1:1.8, more preferably of from 1:0.8 to 1:1.2, and most preferably of 1:0.9 to 1:1.1.

Step (i)

The temperature for step i) is not limiting. However, preferably, the mixture in (i) has a temperature in the range of from 10° C. to 30° C., more preferably from 15° C. to 25° C. and most preferably of 22° C.

In (i) the solvent comprises, and more preferably it is acetone. Preferably, when the solvent in (i) is acetone, the solvent comprises no additional organic solvent, most preferably the solvent in (i) is essentially free of any additional organic solvent.

The concentration of cabozantinib in the solvent is preferably from 0.2 g/mL to 4 g/mL.

Step (ii)

The temperature for step i) is not limiting. However, preferably, the mixture in (ii) has a temperature in the range of from 10° C. to 30° C., more preferably from 15° C. to 25° C. and most preferably of 22° C.

It is preferred that the temperature of the mixture of step (i) is the same as the temperature of the mixture of step (ii).

In (ii) the solvent comprises, and more preferably it is tetrahydrofuran. Preferably, when the solvent in (ii) is tetrahydrofuran, the solvent comprises no additional organic solvent, most preferably the solvent in (ii) is essentially free of any additional organic solvent.

The solvent in (i) and (ii) may be the same or different.

Preferably, the volume of the solvent in (ii) is such that succinic acid may form a slurry or a solution.

Preferably, 0.2 g to 4 g of succinic acid per ml of solvent is used.

Step (iii)

Preferably, the mixture in (iii) has a temperature in the range of from 10° C. to 30° C., more preferably from 15° C. to 25° C. and most preferably of 22° C.

The volume ratio mixture (i):mixture (ii) is from 1:4 to 4:1, preferably from 1:2 to 2:1.

Step (iv)

It has been found that by subjecting the mixture obtained from (iii) to temperature cycling the crystalline forms of the invention are obtained.

Preferably, the upper temperature of a temperature cycle is from 35° C. to 60° C., such as from 35° C. to 45° C., and the lower temperature of a temperature cycle is from 10° C. to 25° C. Preferably, the difference between the upper and the lower temperature in a cycle is at least 10 K, for example at least 15 K, such as preferably 20 K.

Preferably, in an individual cycle the upper temperature is maintained constant for at least 30 min, such as for at least 60 min.

Preferably, in an individual cycle the lower temperature is maintained constant for at least 30 min, such as for at least 60 min.

The heating/cooling rate within a temperature cycle in order to change from the lower temperature to the upper temperature and from the upper temperature to the lower temperature, respectively, is not particularly limited. For example, the heating rate could be from 0.3 K/min to 5 K/min, such as from 1 K/min to 3 K/min.

Preferably, the temperature cycling is carried out in cycles wherein each cycle preferably is in the range of from 2 to 6 h, more preferably in the range of from 3 to 5 h.

Preferably, the temperature cycling comprises at least 4 cycles, preferably at least 12 cycles, more preferably at least 18 cycles.

Preferably or alternatively, the temperature cycling is carried out for the overall period preferably in the range of from 12 to 96 h, more preferably in the range of from 36 to 84 h, even more preferably in the range of from 60 to 72 h.

Preferably, the temperature cycling is carried out in cycle wherein each cycle preferably is in the range of from 3 to 5 h for an overall time of 60 to 72 h.

The temperature cycling may be optionally carried out under stirring.

Seed crystals may be added to any crystallization mixture to promote crystallization. Preferably the seeds are added in (iii) or in (iv), more preferably the are added in (iv). Seeding may be employed to control growth of Form A and Form A-1 or to control the particle size distribution of the crystalline product.

Step (v)

The process according to the invention may further comprise evaporating at least part of the solvents to favor the crystallization of Form A or Form A-1 of the invention Step (v) can be carried out after step (iii) or after (iv) or both after step (iii) and step (iv).

Alternatively or additionally seed crystals may be added in (iii) or in (iv) before carrying out the evaporation to further favor crystallization of Form A or Form A-1 of the invention.

The process may further comprise (vi) isolating at least a part of the crystalline form of step (iv) from its mother liquor.

Step (vi)

The obtained crystalline form may optionally be isolated or collected by any conventional method such as filtration or centrifugation, most preferably by filtration from the mother liquor.

Preferably, Form A is isolated or collected by any conventional method such as filtration or centrifugation, most preferably by filtration from the mother liquor.

Preferably, Form A-1 is isolated or collected by any conventional method such as filtration or centrifugation, most preferably by filtration from the mother liquor.

The process may further comprise (vii) after (v) or (vi) optionally washing the isolated crystalline form with a solvent Step (vii)

In (vii) the isolated crystalline form, preferably Form A or Form A-1 obtained in (v) or (vi) is washed with a solvent in which Form A or Form A-1 have low or now solubility.

Preferably, the solvent comprises an organic solvent, whereat the organic solvent is selected from alcohols, ketones, nitriles, cyclic ethers or mixtures of two or more of them. More preferably, the solvent comprises a ketone such as acetone or a cyclic ethers such as tetrahydrofuran or an alcohols such as methanol, ethanol, 1-propanol, 2-propanol or mixtures of two or more thereof and most preferably the solvent is acetone or tetrahydrofuran or a mixture thereof. The skilled person will appreciate that washing is carried out with a cold wash solvent so as to minimize mass losses.

The process may further comprise:

(viii) after (iv) or (v) or (vi) optionally drying the isolated crystalline form of the invention obtained in (iv) or (v).

The isolated crystalline form, preferably Form A or Form A-1 can further be dried under gentle conditions. After drying, the dried crystalline form of the invention, preferably Form A or Form A-1 is obtained.

The present invention is directed to Form A or Form A-1 obtainable or obtained according to any of the processes disclosed above.

Pharmaceutical Composition

The present invention is further directed to a pharmaceutical compositions comprising a cabozantinib succinate Form A or cabozantinib acetate Form A-1 and at least a pharmaceutically acceptable excipient. More preferably the pharmaceutical composition of the invention comprises Form A.

The pharmaceutical composition of the invention is preferably an oral dosage form such as tablet, capsule such as hard capsule, syrup, preferably the oral dosage form is a tablet or a capsule, preferably the capsule is a hard capsule.

Preferably the pharmaceutical composition comprises an effective dose of the crystalline form of the invention. Preferably, the effective dose is in the range of 20 to 80 mg of cabozantinib crystalline form of the invention. The effective dose preferably refers to a daily dose.

Hence, preferably the pharmaceutical composition of the invention comprises an effective dose of the Form A of the invention. Preferably, the effective dose of Form A is in the range of 20 to 80 mg. The effective dose preferably refers to a daily dose.

Hence, preferably the pharmaceutical composition comprises an effective dose of the Form A-1 of the invention. Preferably, the effective dose of Form A-1 is in the range of 20 to 80 mg. The effective dose preferably refers to a daily dose.

More preferably, the pharmaceutical composition comprises an effective dose of the Form A of the invention. Preferably, the effective dose of Form A is in the range of 20 to 80 mg. The effective dose preferably refers to a daily dose.

The pharmaceutical composition of the invention, preferably the oral dosage form of the invention comprises an effective amount of Form A or Form A-1 as disclosed above and one or more pharmaceutically acceptable excipients such as filler, disintegrant, glidant, lubricant, binder; preferably the oral dosage form of the invention comprises an effective amount of Form A or Form A-1, filler, disintegrant, glidant and lubricant.

A preferred capsule of the present invention comprises an effective amount of Form A or A-1, a filler, a disintegrant, a glidant and a lubricant. Preferably the filler is a silicified microcrystalline cellulose, preferably the disintegrant is croscarmellose sodium or sodium starch glycolate or mixture thereof, preferably the glidant is silica colloidal anhydrous, and preferably the lubricant is stearic acid. Preferably the empty capsule is of gelatin and optionally comprises colorants, opacifier and ink. Black iron oxide and red iron oxide are examples of colorants according to the invention. Titanium dioxide can be used as opacifier.

The present invention further relates to Form A or Form A-1 of the invention or to the pharmaceutical composition comprising Form A or Form A-1 of the invention for use as a medicament, preferably as an anti-cancer medicament.

The present invention relates to the Form A or Form A-1 of the invention or to the pharmaceutical composition comprising Form A or Form A-1 of the invention for use in the treatment or prevention of cancer, preferably of a thyroid cancer, wherein preferably the thyroid cancer is a metastatic medullary thyroid cancer.

Advantages

The solubility of Form A is of 0.164 mg/ml as measured by HPLC analysis, thus showing an improved solubility compared to cabozantinib malate.

Based on its DVS isotherm, cabozantinib succinate Form A of the present invention is less hygroscopic than cabozantinib malate. For example, the DVS isotherm measured at a relative humidity between 20 and 70% at (25.2±1.0)° C. shows that cabozantinib succinate Form A takes up only about 0.03 weight-% water, whereat the weight gain of L-malate is of about 0.3 weight-% and thus 10-fold higher. Post-DVS XRPD analysis showed cabozantinib succinate Form A to have remained crystalline and consistent with the input form. The comparison of the DVS isotherm clearly shows that Form A is a non-hygroscopic form with a hygroscopicity even lower than the hygroscopicity of cabozantinib (L)-malate.

The TG/DTA analysis of cabozantinib succinate Form A of the present invention showed a weight loss of less than ca. 0.6 weight-% below ca. 173° C. and ca 1 weight % weight loss corresponding to the endotherm in the DTA trace at ca. 173° C. indicating that form A is an anhydrous salt form in nature.

Based on its DVS isotherm, cabozantinib acetate Form A-1 of the present invention is less hygroscopic than cabozantinib malate. For example, between 20 and 70% relative humidity at (25.0±1.0)° C. Form A-1 takes up only about 0.1 weight % of water, whereas the weight gain of cabozantinib malate is about 0.3 weight-%. Post-DVS XRPD analysis showed Form A-1 to have remained crystalline and consistent with the input form.

TABLE 2

Comparison of physicochemical properties of cabozantinib succinate Form A and cabozantinib acetate Form A-1 of the invention with cabozantinib (L)-malate
Table 2 summarizes the aforementioned data for better comparison.

| Analytical Method | (L)-malate | Form A (present invention) | Form A-1 (present invention) |
|---|---|---|---|
| TG/DTA | 1.2 weight-% loss below ca. 178° C. and 1% loss corresponding to the endotherm in DTA trace at ca. 178° C. | 0.6 weight-% loss below ca 173° C. and 1 weight-% loss at ca. 173° C. | 0.3 weight-% loss below 100° C. and 7 weight-% loss between 100 and 150° C. corresponding to the endotherm in DTA trace at 120° C. |
| DVS between 20%-70% RH | 0.3 weight-% water up take | 0.03 weight-% water up take | 0.1 weight-% water up take |

Cabozantinib succinate Form A comprises crystals having a compact shape and therefore shows good filterability. Such a shape is highly appreciated by formulation scientists as it usually shows good powder properties such as flow properties and compressibility and is therefore easy to handle in pharmaceutical processes. Furthermore, Form A, as indicated above, shows an improved solubility and a lower hygroscopicity with respect to cabozantinib (L)-malate, that renders Form A an attractive form in the pharmaceutical field.

Form A-1 has been shown to be non-hygroscopic and anhydrous in nature.

All in all Form A and Form A-1 show physicochemical properties, which render them a particular suitable crystalline form of cabozantinib for pharmaceutical purposes. Especially their inertness to water vapour favors these forms for pharmaceutical production processes. Form A further shows an increased solubility, high chemical stability and its appreciated morphology which further favor this form for pharmaceutical production processes.

Figure 5:
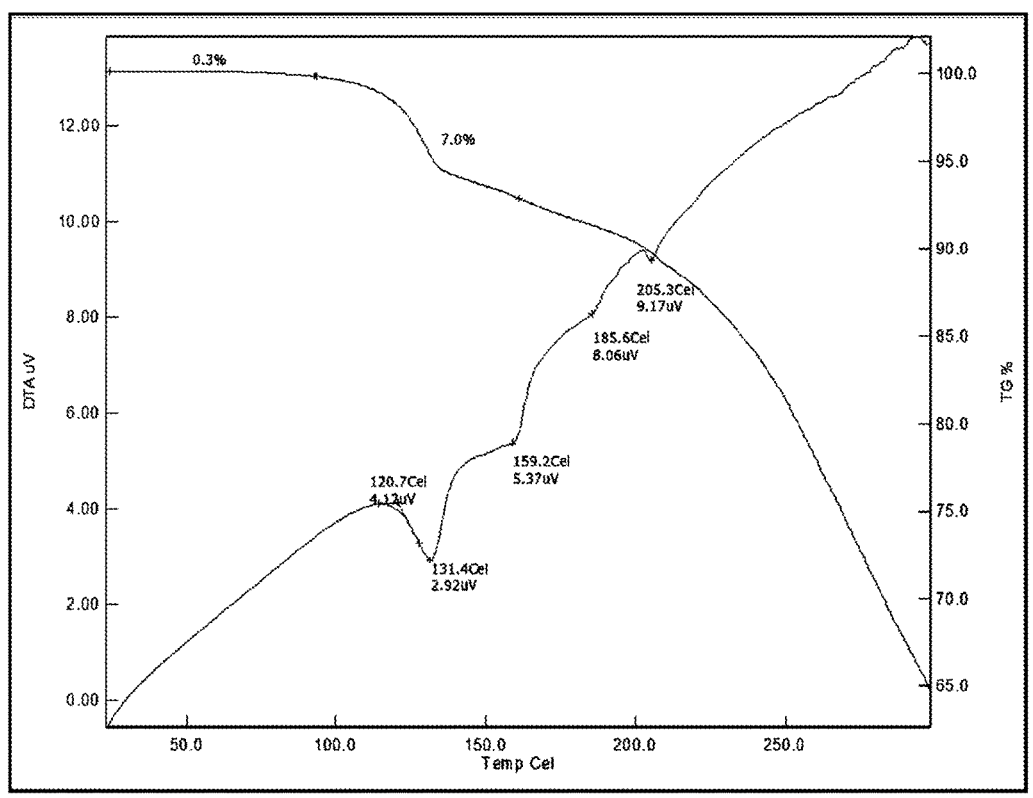
FIG. 5: Representative TG/DTA curve of the crystalline Form A-1 of cabozantinib acetate according to the present invention.

The present invention is further illustrated by the following embodiments and combinations of embodiments resulting from the given dependencies and back-references:

0. N-{4-[(6,7-dimethoxy-4-quinolinyl)oxy]phenyl}-N'-(4-fluorophenyl)-1,1-cyclopropanedicarboxamide succinate.
1. A crystalline form of N-{4-[(6,7-dimethoxy-4-quinolinyl)oxy]phenyl}-N'-(4-fluorophenyl)-1,1-cyclopropanedicarboxamide succinate characterized by a powder X-ray diffractogram (XRPD) comprising reflections at 2-Theta angles of (8.5±0.2°), (10.4±0.2°), (19.1±0.2°), (21.4±0.2°), (24.8±0.2°) when measured at 20° C. with Cu-Kalpha radiation having a wavelength of 0.15419 nm, in particular when measured as disclosed in reference example A) herein.
2. The crystalline form of embodiment 0 or 1, characterized by a XRPD comprising reflections at 2-Theta angles of (8.5±0.2°), (10.4±0.2°), (19.1±0.2°), (21.4±0.2°), (24.8±0.2°), (25.8±0.2°) when measured at 20° C. with Cu-Kalpha radiation having a wavelength of 0.15419 nm, in particular when measured as disclosed in reference example A) herein.
3. The crystalline form of embodiment 1 or 2, characterized by having a XRPD comprising additional one or more reflections at 2-Theta angles selected from the group of (23.2±0.2°) and (23.4±0.2°).
4. The crystalline form of any one of embodiments 1 to 3, characterized by having a XRPD comprising additional one or more reflections at 2-Theta angles selected from the positions listed in table 1.
5. The crystalline form of any one of embodiments 1 to 3, characterized by having a XRPD comprising additional five or more reflections at 2-Theta angles selected from the positions listed in table 1.
6. The crystalline form of any one of embodiments 1 to 3, characterized by having a XRPD comprising reflections at 2-Theta angles at all bold positions listed in table 1, preferably comprising reflections at 2-Theta angles at all of the positions listed in table 1.
7. The crystalline form of any one of embodiments 0 or 1 to 6, characterized by a XRPD being essentially the same as displayed in FIG. 1.
8. The crystalline form of any one of embodiments 0 or 1 to 7, characterized by having a TG/DTA curve showing a weight loss of at most 1.2 weight-% based on the weight of the crystalline form in the temperature range of from 25° C. to 173° C., and when measured at a heating rate of 10° C./min, in particular as disclosed in reference example B) herein.
9 The crystalline form of embodiment 8, wherein the weight loss is in the range of from 0.15 to 0.80 weight-% based on the weight of the crystalline form.
10. The crystalline form of any one of embodiments 0 or 1 to 9 characterized by having a TG/DTA curve being essentially the same as displayed in FIG. 2, when measured at a heating rate of 10° C./min, in particular as disclosed in reference example B) herein.
11. The crystalline form of any one of embodiments 0 or 1 to 10 characterized by showing a weight gain of at most 0.2 weight-% based on the weight of the crystalline form, as determined by dynamic vapor sorption (DVS) in the range of from 20 to 70% relative humidity at a temperature of (25.0±0.2)° C. in particular when measured as disclosed in reference example C) herein.
11' The crystalline form of embodiment 11, wherein the weight gain is at most 0.1%.
11". The crystalline form of embodiment 11 or 11', wherein the weight gain is at most 0.06%.
11'''. The crystalline form of any one of embodiments 0 or 1 to 11", characterized by a DVS isotherm being essentially the same as displayed in FIG. 3, in particular when measured as disclosed in reference example C) herein.
12. The crystalline form of any of the embodiments 1 to 11''', wherein the molar ratio of the N-{4-[(6,7-dimethoxy-4-quinolinyl)oxy]phenyl}-N'-(4-fluorophenyl)-1,1-cyclopropanedicarboxamide relative to the succinic acid is in the range of from 1:0.5 to 1:2, more preferably in the range of from 1:0.7 to 1:1.5 and most preferably in the range of from 1:1 to 1:1.2.
13. The crystalline form of anyone of embodiments 1 to 12, characterized by a water content equal or less than 0.20 weight-%, preferably equal or less than 0.15%, based on the total weight of the crystalline form, as measured by KF analysis, in particular as disclosed in reference example G) herein
13' The crystalline form of anyone of embodiments 1 to 13 which is anhydrous.
13". The crystalline form of anyone of embodiments 1 to 13' which is non-hygroscopic.
0'. N-{4-[(6,7-dimethoxy-4-quinolinyl)oxy]phenyl}-N'-(4-fluorophenyl)-1,1-cyclopropanedicarboxamide acetate.
15. A crystalline form of the N-{4-[(6,7-dimethoxy-4-quinolinyl)oxy]phenyl}-N'-(4-fluorophenyl)-1,1-cyclopropanedicarboxamide acetate characterized by a XRPD comprising reflections at 2-Theta angles of (11.3±0.2°), (12.4±0.2°), (15.4±0.2°) when measured at a temperature of 20° C. with Cu-Kalpha radiation having a wavelength of 0.15419 nm, in particular as disclosed in reference example A) herein.
16. The crystalline form of embodiment 0' or 15, characterized by a XRPD comprising reflections at 2-Theta angles of (11.3±0.2°), (12.4±0.2°), (15.4±0.2°), (24.5±0.2°) when measured at a temperature of 20° C. with Cu-Kalpha radiation having a wavelength of 0.15419 nm, in particular as disclosed in reference example A) herein.
17. The crystalline form of embodiment 15 or 16, characterized by having a XRPD comprising additional one or more reflections at 2-Theta angles selected from the group of (21.5±0.2°), (22.6±0.2°).
18. The crystalline form of any one of embodiments 0' or 15 to 17, characterized by having a XRPD comprising five or more reflections at 2-Theta angles selected from the group of Form A-1 reflections as listed in table 1.
19. The crystalline form of any one of embodiments 15 or 18, characterized by having a XRPD comprising reflections at 2-Theta angles at all bold positions listed in table 1, preferably comprising reflections at 2-Theta angles at all of the positions listed in table 1.
20. The crystalline form of any one of embodiments 0' or 15 to 19, characterized by a XRPD being essentially the same as displayed in FIG. 5, when measured at a temperature of 20° C. with Cu-Kalpha radiation having a wavelength of 0.15419 nm in particular as disclosed in reference example A) herein.
22. The crystalline form of any one of embodiments 0' or 15 to 21, characterized by having a TG/DTA curve showing a weight loss of at most 0.5 weight-% based on the weight of the crystalline formin the temperature range of from 25° C. to 100° C. when measured at a heating rate of 10° C./min, in particular as disclosed in reference example B) herein.
23. The crystalline form of embodiment 22, wherein the weight loss is in the range of from 0.2 to 0.4 weight-%.
24. The crystalline form of any one of embodiments 0' or 15 to 23, characterized by having a TG/DTA curve being essentially the same as displayed in FIG. 5 when measured at a heating rate of 10° C./min, in particular as disclosed in reference example B) herein.
25. The crystalline form of to any one of embodiments 0' or 15 to 24, characterized by showing a weight gain of at most 0.5 weight-% based on the weight of the crystalline form, as determined by dynamic vapor sorption (DVS) in the range of from 20 to 70% relative humidity at a temperature of (25.0±0.2)° C., in particular when measured as disclosed in reference example C) herein.

25'. The crystalline form of any one of embodiments 0' or 15 to 25 characterized by a dynamic vapor sorption (DVS) isotherm being essentially the same as displayed in FIG. 6 as determined in the range of from 20 to 70% of relative humidity at a temperature of (25.0±0.2)° C. in particular as disclosed in reference example C) herein.

26. The crystalline form of any one of embodiments 0' or 15 to 25', wherein the molar ratio of N-{4-[(6,7-dimethoxy-4-quinolinyl)oxy]phenyl}-N'-(4-fluorophenyl)-1,1-cyclopropanedicarboxamide relative to acetate is in the range of from 1:0.5 to 1:2, more preferably in the range of from 1:0.7 to 1:1.5 and most preferably in the range of from 1:1 to 1:1.2.

27. The crystalline form of any one of embodiments 0' or 1 to 26, in substantially pure form.

28. A pharmaceutical composition comprising an effective amount of the crystalline form of any one of embodiments 1 to 27 and at least one pharmaceutically acceptable excipient.

28' The pharmaceutical composition of embodiment 86, wherein the crystalline form is according to embodiment 1 to 14 and 27.

28" The pharmaceutical composition of embodiment 28', wherein the crystalline form is according to embodiment 15 to 27.

29. The pharmaceutical composition of any one of embodiments 28 to 28", wherein the at least one pharmaceutically acceptable excipient is selected from a filler, a disintegrant, a glidant and a lubricant.

30. The pharmaceutical composition of any one of embodiments 28 to 29, which is a pharmaceutical composition for oral administration.

31. The pharmaceutical composition of embodiment 30, wherein the pharmaceutical composition for oral administration is a tablet or a capsule, preferably the capsule is a hard gelatine capsule.

32. The pharmaceutical composition of any one of embodiments 29 to 31 wherein the effective amount of the crystalline form is in the range of 20 to 80 mg.

33. A method of treating or preventing cancer, preferably a thyroid cancer, more preferably metastatic medullary thyroid cancer comprising administering the crystalline form of any one of embodiments 1 to 27 or the pharmaceutical composition of any one of embodiments 28 to 32 to a patient in need thereof.

The following non-limiting examples are illustrative for the disclosure and are not to be construed to be limiting for the scope of the claims.

EXAMPLES

Reference Examples: Determination of Physical Parameters
A) X-ray Powder Diffraction Pattern (XRPD)

XRPD analysis was carried out on a Siemens D5000 diffractometer, scanning the samples between 3 and 50 or 30°2-theta. For samples of less than 100 mg, 10-20 mg of material was gently compressed onto a glass disc inserted into an XRPD sample holder. For samples of more than 100 mg, ca. 100 mg of material was gently compressed into a plastic XRPD sample holder to ensure a smooth sample surface, just above the level of the sample holder. The sample was then loaded into the diffractometer running in reflection mode and analyzed using the following experimental conditions.

| Raw Data Origin | SiemensbinaryV2 (.RAW) |
|---|---|
| Start Position [°2Th.] | 3.0000 |
| End Position [°2Th.] | 30.000 or 50.000 |
| Step Size [°2Th.] | 0.0200 |
| Scan Step Time [s] | 1 |
| Scan Type | Continuous |
| Offset [°2Th.] | 0.0000 |
| Divergence Slit Type | Fixed |
| Divergence Slit Size [°] | 2.0000 |
| Specimen Length [mm] | various |
| Receiving Slit Size [mm] | 0.2000 |
| Measurement Temperature [° C.] | 20.00 |
| Anode Material | Cu |
| K-Alpha1,2 | 0.15419 |
| K-Beta [Å] | 1.39225 |
| K-A2/K-A1 Ratio | 0.50000 |
| (nominal) Generator Settings | 40 mA, 40 kV |
| Diffractometer Type | d5000 |
| Goniometer Radius [mm] | 217.50 |
| Incident Beam Monochromator | No |
| Diffracted Beam Monochromator | Graphite |
| Spinning | No |

B) Organic Solvent Content: Thermogravimetric Analysis (TGA)

Approximately, 5-10 mg of material was accurately weighed into an open aluminium pan and loaded into a simultaneous thermogravimetric/differential thermal analyser (TG/DTA) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 cm$^3$/min.

C) Water Content: Dynamic Vapour Sorption (DVS)

Approximately 10-20 mg of sample was placed into a vapour sorption balance pan and loaded into a DVS-1 dynamic vapour sorption balance by Surface Measurement Systems. The sample was subjected to a ramping profile from 20-90% relative humidity (RH) at 10% increments, maintaining the sample at each step until a stable weight had been achieved (99.5% step completion). After completion of the sorption cycle, the sample was dried using the same procedure, but all the way down to 0% RH and finally taken back to the starting point of 20% RH. The weight change during the sorption/desorption cycles were plotted, allowing for the hygroscopic nature of the sample to be determined.

D) Polarised Light Microscopy (PLM)

The presence of birefringence was determined using an Olympus BX50 polarising microscope, equipped with a Motic camera and image capture software (Motic Images Plus 2.0). All images were recorded using the 20× objective lens, unless otherwise stated.

E) High Performance Liquid Chromatography-Ultraviolet Detection (HPLC-UV)

HPLC analysis was performed according to the following conditions:

Instrument: Agilent 1100

Column: Grace Smart RP 185µ 150×4.6 mm

Column Temperature: 30° C. UV wavelength: 249 nm

Injection Volume: 10 µl

Flow Rate: 1.2 ml/min

Mobile Phase A: 0.1% Phosphoric acid
Mobile Phase B: 0.1% Phosphoric acid in acetonitrile
Gradient program:

| Time (minutes) | Solvent B [%] |
|---|---|
| 0 | 5 |
| 30 | 90 |
| 30.1 | 5 |
| 40 | 5 |

G) Karl Fischer Coulometric Titration (KF)

Ca. 10-20 mg of solid material was accurately weighed into a container and the weight noted. The solid was then manually introduced into the titration cell of a Mettler Toledo C30 Compact Titrator. The titration was initiated once the sample had fully dissolved in the cell.

The vial was back-weighed after the addition of the solid and the weight of the added solid entered into the instrument. The water content was calculated automatically by the instrument as a percentage and the data printed.

H) Aqueous Solubility Measurements

Each salt was individually slurried in deionized water and subjected to shaking for ca. 24 h at ambient temperature (ca. 22° C.). The resulting saturated solutions were filtered and analyzed by HPLC analysis. XRPD analysis was carried out on any solid retained after the solubility experiment.

Example 1

Preparation of Cabozantinib Form A (Succinate)

0.5 g of cabozantinib free base obtained according to WO 2010/083414, preparative example 1.6., were dissolved in 0.5 mL acetone. Approximately one equivalent of succinic acid was slurried in 0.5 mL tetrahydrofuran. The cabozantinib solution was added to the succinic acid slurry. Whilst stirring, the resulting mixture was temperature cycled between 22 and 40° C. in 4 hour cycles for ca. 24 h. A further 0.5 mL of THF and 0.5 mL of acetone were added to the mixture and the mixture was then cycled between 22 and 40° C. in 4 hour cycles for ca. 72 h. The slurry was filtered and the solid dried in a dessicator under vacuum at ambient for c.a. 1 day.

The XRPD diffractogram (FIG. 1) of the succinate Form A indicated the material to be crystalline.

Figure 7:
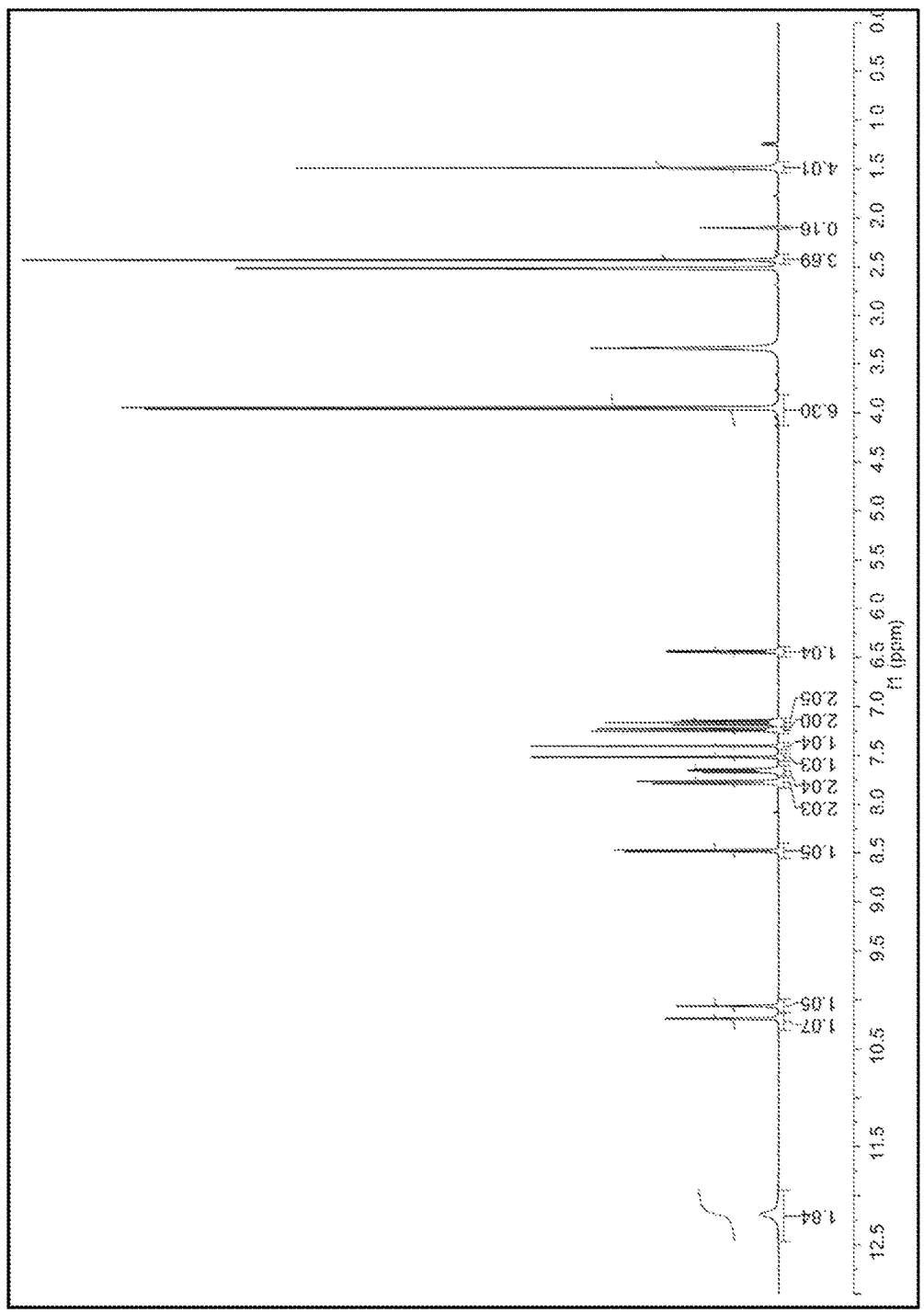
FIG. 7: $^1$H NMR of crystalline form A of cabozantinib succinate

$^1$H NMR spectroscopy showed a cabozantinib:succinic acid molar ratio of ca. 1:1 (FIG. 7).

The TG/DTA analysis (FIG. 2) showed a ca. 0.6 weight-% loss below ca. 173° C. and ca. 1 weight-% loss corresponding to the endotherm in the DTA trace at ca. 173° C., indicating a anhydrous salt form.

The crystalline succinate salt of cabozantinib was found to be non-hygroscopic with a water up-take of ca. 0.03 weight-% between 20% and 70% RH by DVS analysis (FIG. 3). Post-DVS XRPD analysis showed the material to have remained crystalline and was consistent with the input form The aqueous solubility of the succinate salt of cabozantinib was found to be 0.164 mg/ml by HPLC analysis. After the solubility experiment, the salt was found to be consistent with the input succinate salt.

Example 2

Preparation of Cabozantinib Form A-1 (Acetate)

0.2 g of cabozantinib free base were dissolved in 0.1 mL acetone. Approximately 1 equivalent of acetic acid was dissolved in 0.1 mL tetrahydrofuran. The cabozantinib solution was added to the acetic acid solution. The solvent was evaporated at room temperature. The obtained solid mass was re-dissolved in 0.1 mL THF:acetone (1:1) by stirring and heating at 40° C. for 2 to 3 min. The resulting solution was then allowed to evaporate at room temperature and the resulting solid was dried under vacuum at room temperature. Crystalline cabozantinib acetate was obtained.

The XRPD diffractogram (FIG. 5) of the product indicated the material to be crystalline.

Figure 8:
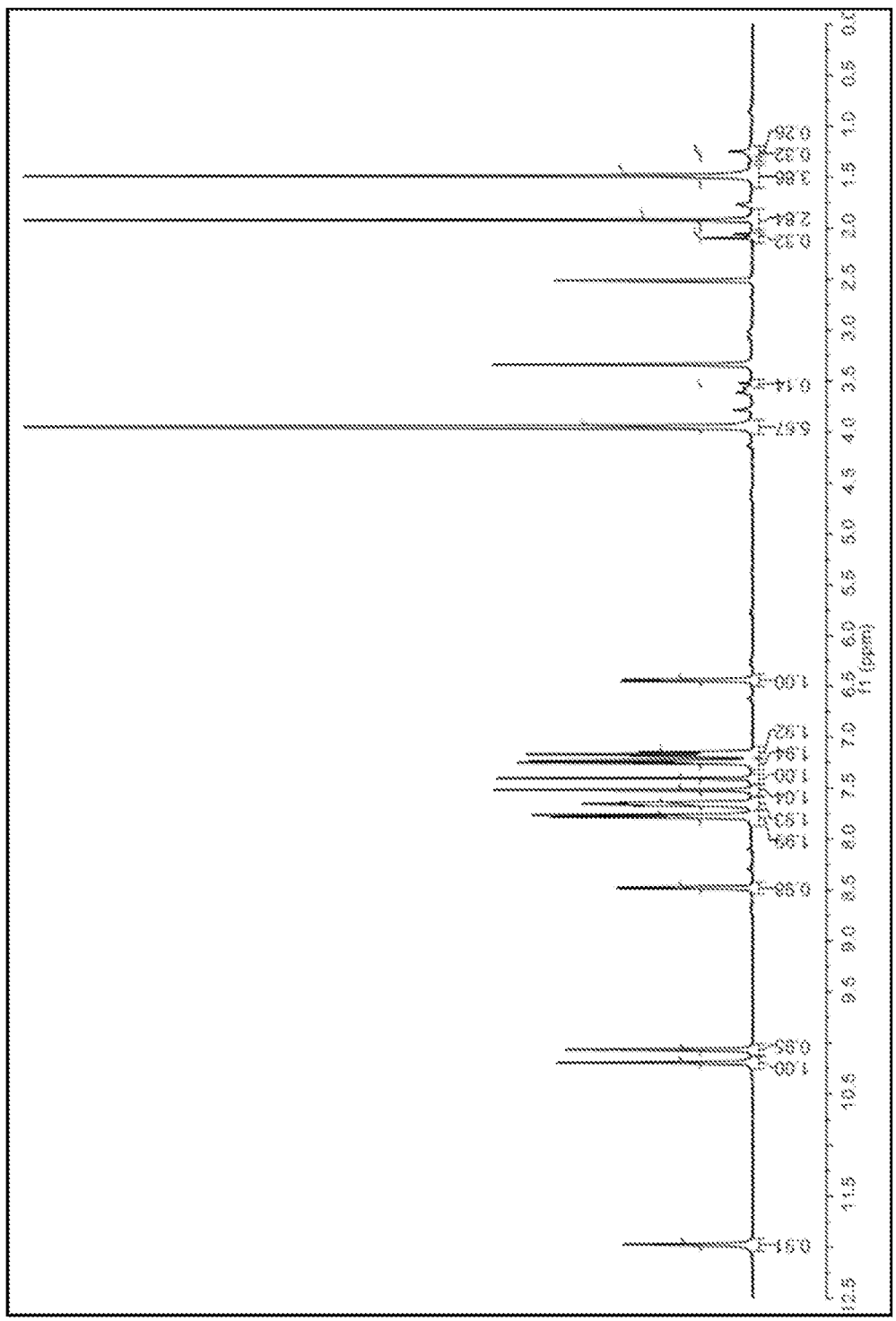
FIG. 8: $^1$H NMR of crystalline form A-1 of cabozantinib acetate

$^1$H NMR spectroscopy revealed a cabozantinib: acetic acid molar ratio of 1:1 (FIG. 8). Only traces of acetone and tetrahydrofuran were detected.

The TG/DTA analysis (FIG. 6) showed 0.3 weight-% weight loss below 100° C. and ca 7 weight-% weight loss between 100 and 150° C. corresponding to endotherm DTA trace at 120° C.

The acetate salt was found to be non-hygroscopic with a water up take of c.a. 0.1 weight-% observed between 20% and 70% RH by DVS analysis. Post-DVS XRPD analysis showed that the material remained crystalline.

The examples 3 and 4 below are specific and preferred examples for capsules and tablets prepared from a crystalline form of the present invention. One skilled in the art will appreciate that changes and modifications to the described examples can be practices within the scope of the appended claims.

Example 3

Capsule Composition Comprising Crystalline Cabozantinib Succinate Form A

Drug substance and excipients are screened and blended using typical manufacturing equipment. Pharmaceutical capsule compositions such as exemplified below are then prepared from the blend.

A pharmaceutical capsule composition comprising 20 mg cabozantinib in form of its non-hygroscopic succinate salt Form A according to Table 3.

TABLE 3

| Ingredient | mg/unit dose |
|---|---|
| Cabozantinib succinate Form A | 24.7 |
| Silicified microcrystalline Cellulose | 197.05 |
| Croscarmellose sodium | 12.5 |
| Sodium starch glycolate | 12.5 |
| Fumed Silica | 0.75 |
| Stearic acid | 2.5 |
| Total Fill Weight | 250 |

A pharmaceutical capsule composition comprising 80 mg cabozantinib in form of its non-hygroscopic succinate salt Form A according Table 4.

TABLE 4

| Ingredient | mg/unit dose |
|---|---|
| Cabozantinib succinate Form A | 98.8 |
| Silicified microcrystalline Cellulose | 152.53 |
| Croscarmellose sodium | 14.5 |
| Sodium starch glycolate | 14.5 |

TABLE 4-continued

| Ingredient | mg/unit dose |
|---|---|
| Fumed Silica | 0.87 |
| Stearic acid | 5.8 |
| Total Fill Weight | 287 |

A pharmaceutical capsule composition comprising 80 mg cabozantinib in form of its non-hygroscopic succinate salt Form A according Table 5.

TABLE 5

| Ingredient | mg/unit dose |
|---|---|
| Cabozantinib succinate Form A | 98.8 |
| Silicified microcrystalline Cellulose | 76.6 |
| Croscarmellose sodium | 10.0 |
| Sodium starch glycolate | 10.0 |
| Fumed Silica | 0.6 |
| Stearic acid | 4.0 |
| Total Fill Weight | 200 |

Example 4

Tablet Compositions Comprising Crystalline Cabozantinib Succinate Form A

Drug substance and excipients are screened and blended using typical manufacturing equipment. Tablets such as exemplified below are then prepared from the blend.

A tablet composition comprising 20, 40, 60, or 80 mg cabozantinib in form of its non-hygroscopic succinate salt Form A according Table 6

TABLE 6

| Ingredient | % w/w |
|---|---|
| Cabozantinib succinate Form A | 30.9 |
| Microcrystalline Cellulose | q.s. |
| Hydroxypropyl Cellulose | 3 |
| Poloxamer | 0-3 |
| Croscarmellose Sodium | 6.2 |
| Colloidal Silicon Dioxide | 0.5 |
| Magnesium Stearate | 0.75 |
| Total | 100.00 |

A tablet comprising 20, 40, 60, or 80 mg cabozantinib in form of its non-hygroscopic succinate salt Form A according to Table 7.

TABLE 7

| Ingredient | Function | % w/w |
|---|---|---|
| Cabozantinib succinate Form A | Active Ingredient | 30.9 |
| Microcrystalline Cellulose (Avicel PH-102) | Filler | 39.4 |
| Lactose Anhydrous (60M) | Filler | 19.65 |
| Hydroxypropyl Cellulose (EXF) | Binder | 3.0 |

TABLE 7-continued

| Ingredient | Function | % w/w |
|---|---|---|
| Croscarmellose Sodium (Ac-Di-Sol) | Disintegrant | 6.0 |
| Colloidal Silicon Dioxide | Glidant | 0.3 |
| Magnesium Stearate | Lubricant | 0.75 |
| Opadry Yellow Film Coating which includes: | | |
| HPMC 2910/Hypromellose 6 cp | Film Coating | 4.00 |
| Titanium dioxide | | |
| Triacetin | | |
| Iron Oxide Yellow | | |

The invention claimed is:

1. A crystalline form of N-{4-[(6,7-dimethoxy-4-quinolinyl) oxy]phenyl}-N'-(4-fluorophenyl)-1,1-cyclopropanedicarboxamide succinate characterized by a powder X-ray diffractogram comprising reflections at 2-Theta angles of (8.5±0.2)°, (10.4±0.2)°, (19.1±0.2)°, (21.4±0.2)°, (24.8±0.2)°, when measured at a temperature of 20° C. and with Cu-Kalpha radiation having a wavelength of 0.15419 nm.

2. The crystalline form of claim 1, characterized by having a XRPD comprising at least one additional reflection at 2-Theta angles selected from the group of (21.5±0.2)°, (22.6±0.2)°.

3. The crystalline form of claim 1 characterized by showing a weight gain of at most 0.2 weight-% based on the weight of the crystalline form, as determined by dynamic vapor sorption (DVS) in the range of from 20 to 70% relative humidity at a temperature of (25.0±0.2)° C.

4. The crystalline form of claim 1, wherein the molar ratio of the N-{4-[(6,7-dimethoxy-4-quinolinyl)oxy]phenyl}-N'-(4-fluorophenyl)-1,1-cyclopropanedicarboxamide relative to the succinic acid is in the range of from 1:0.7 to 1:1.5.

5. A crystalline form of N-{4-[(6,7-dimethoxy-4-quinolinyl) oxy]phenyl}-N'-(4-fluorophenyl)-1,1-cyclopropanedicarboxamide acetate characterized by a powder X-ray diffractogram comprising reflections at 2-Theta angles of (11.3±0.2)°, (12.4±0.2)°, (15.4±0.2)°, when measured at a temperature of 20° C. with Cu-Kalpha radiation having a wavelength of 0.15419 nm.

6. The crystalline form of claim 5, characterized by having a XRPD comprising at least one additional reflection at 2-Theta angles selected from the group of (21.5±0.2)°, (22.6±0.2)°.

7. The crystalline form of claim 5, characterized by showing a weight gain of at most 0.5 weight-% based on the weight of the crystalline form, as determined by dynamic vapor sorption (DVS) in the range of from 20 to 70% relative humidity at a temperature of (25.0±0.2)° C.

8. The crystalline form according to claim 5, wherein the molar ratio of N-{4-[(6,7-dimethoxy-4-quinolinyl)oxy]phenyl}-N'-(4-fluorophenyl)-1,1-cyclopropanedicarboxamide relative to acetate is in the range of from 1:0.7 to 1:1.5.

9. A pharmaceutical composition comprising an effective amount of the crystalline form according to claim 1 and at least one pharmaceutically acceptable excipient.

10. A method of treating thyroid cancer, comprising administering the crystalline form of claim 1 to a patient in need thereof.

\* \* \* \* \*